US012721859B1

(12) United States Patent
Chaubal et al.

(10) Patent No.: US 12,721,859 B1
(45) Date of Patent: Sep. 1, 2026

(54) PHARMACEUTICALLY ACCEPTABLE READY-TO-USE FERRIC CARBOXYMALTOSE COMPOSITIONS

(71) Applicants: Baxter International Inc., Deerfield, IL (US); Baxter Healthcare SA, Glattpark (CH)

(72) Inventors: Mahesh V Chaubal, Kildeer, IL (US); Jason Robert Mantei, Volo, IL (US); Kelly Ann Parker, Buffalo Grove, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 19/084,135

(22) Filed: Mar. 19, 2025

(51) Int. Cl.
*A61K 31/7135* (2006.01)
*A61J 1/10* (2006.01)
*A61J 1/20* (2006.01)

(52) U.S. Cl.
CPC ............. *A61K 31/7135* (2013.01); *A61J 1/10* (2013.01); *A61J 1/2079* (2015.05)

(58) Field of Classification Search
CPC ............ A61K 31/7135; A61J 1/20; A61J 1/10
See application file for complete search history.

(56) References Cited

U.S. PATENT DOCUMENTS 7,612,109 B2 11/2009 Geisser et al.
7,754,702 B2 7/2010 Helenek et al.
8,263,564 B2 9/2012 Reim et al.
8,263,577 B2 9/2012 Reim et al.
8,431,549 B2 4/2013 Helenek et al.
8,679,851 B2 3/2014 Fang et al.
8,722,101 B2 5/2014 Tanner-Baumgartner et al.
8,895,612 B2 11/2014 Helenek et al.
9,376,505 B2 6/2016 Geisser et al.
10,478,450 B2 11/2019 Helenek et al.
10,519,252 B2 12/2019 Geisser et al.
11,020,369 B2 6/2021 Christensen et al.
11,111,261 B2 9/2021 Christensen et al.
11,123,321 B2 9/2021 Geisser et al.
11,291,645 B2 4/2022 Geisser et al.
11,344,568 B2 5/2022 Helenek et al.
11,364,260 B2 6/2022 Helenek et al.
11,406,656 B2 8/2022 Helenek et al.
11,433,091 B2 9/2022 Helenek et al.
11,447,513 B2 9/2022 Kovi et al.
11,478,502 B2 10/2022 Helenek et al.
11,590,097 B2 2/2023 Geisser et al.
11,731,998 B2 8/2023 Suen et al.
11,806,329 B2 11/2023 Christensen et al.
2006/0116349 A1 6/2006 Helenek et al.
2007/0010700 A1* 1/2007 Bensmann ......... B65D 23/0821 588/1
2008/0234226 A1 9/2008 Erichsen et al.
2012/0214986 A1 8/2012 Mohan Rao et al.
2014/0162974 A1 6/2014 Bregman et al.
2022/0041640 A1 2/2022 Christensen et al.
2023/0084291 A1* 3/2023 James ................. A61K 9/0019 514/502
2023/0181525 A1* 6/2023 Akasapu ................ A61K 47/02 514/474
2023/0201140 A1* 6/2023 Nayani ................. A61K 47/02 514/653
2023/0270671 A1* 8/2023 Shah ....................... A61K 9/08 424/400
2023/0290882 A1 9/2023 Hoang et al.

FOREIGN PATENT DOCUMENTS

AU 2013206429 7/2013
AU 2016205002 8/2016
AU 2018202715 5/2018

(Continued)

OTHER PUBLICATIONS

Fütterer, S. Nanoparticular Iron Complex Drugs for Parenteral Administration: Physicochemical Characterization, Biological Distribution and Pharmacological Safety.(2014).
INJECTAFER® (ferric carboxymaltose injection) For intravenous use; label (2013).
Jahn,et al. A comparative study of the physicochemical properties of iron isomaltoside 1000 (Monofer (R)), a new intravenous iron preparation and its clinical implications. European journal of pharmaceutics and biopharmaceutics : official journal of Arbeitsgemeinschaft für Pharmazeutische Verfahrenstechnik e.V. 78. 480-91. (2011).
Koskenkorva-Frank et al. The complex interplay of iron metabolism, reactive oxygen species, and reactive nitrogen species: insights into the potential of various iron therapies to induce oxidative and nitrosative stress. Free Radic Biol Med. Dec. 2013;65:1174-1194. (2013).

(Continued)

*Primary Examiner* — Shirley V Gembeh
(74) *Attorney, Agent, or Firm* — K&L Gates LLP

(57) ABSTRACT

A pharmaceutical product includes a sealed container and further includes a pharmaceutically suitable ready-to-use ferric carboxymaltose premix composition in the sealed container. The ferric carboxymaltose premix composition contains water, sodium chloride, and ferric carboxymaltose in an amount that includes about 2.0 mg to about 4.0 elemental iron/mL of the composition, preferably about 3.0 mg elemental iron/mL of the composition. The ferric carboxymaltose premix composition is stable in the sealed container at room-temperature (RT) for at least one month. A method of preparing the pharmaceutical product includes: (i) dissolving ferric carboxymaltose in water to form a concentrate; (ii) adjusting the pH of the concentrate to 5.0 to 7.0, preferably about 6.0; (iii) subjecting the pH-adjusted concentrate to addition of thermal energy; (iv) diluting the heat-treated concentrate in the presence of sodium chloride, and adjusting the pH to 5.0 to 7.0, preferably about 6.0, to form the ferric carboxymaltose premix composition; (v) aseptically filling the ferric carboxymaltose premix composition into the container; and (vi) sealing the container.

8 Claims, 9 Drawing Sheets

(56) References Cited

FOREIGN PATENT DOCUMENTS

| | | |
|---|---|---|
| CN | 1771044 | 5/2006 |
| CN | 105125578 | 12/2015 |
| CN | 105520955 | 4/2016 |
| CN | 106236707 | 12/2016 |
| CN | 106727662 | 5/2017 |
| CN | 106977621 | 7/2017 |
| CN | 108129582 | 6/2018 |
| CN | 108498539 | 9/2018 |
| CN | 111077252 | 4/2020 |
| CN | 113004428 | 6/2021 |
| CN | 113004429 | 6/2021 |
| CN | 113018255 | 6/2021 |
| CN | 113018256 | 6/2021 |
| CN | 115177625 | 10/2022 |
| CN | 115322265 | 11/2022 |
| CN | 115364114 | 11/2022 |
| CN | 115368477 | 11/2022 |
| CN | 115368478 | 11/2022 |
| CN | 115403675 | 11/2022 |
| CN | 117343205 | 1/2024 |
| CN | 117843819 | 4/2024 |
| CN | 118085305 | 5/2024 |
| EP | 3339329 | 6/2018 |
| WO | 2004037865 | 5/2004 |
| WO | 2006084782 | 8/2006 |
| WO | 2007023154 | 3/2007 |
| WO | 2007055804 | 5/2007 |
| WO | 2007081744 | 7/2007 |
| WO | 2008087135 | 7/2008 |
| WO | 2008145586 | 12/2008 |
| WO | 2011055374 | 5/2011 |
| WO | 2011069347 | 6/2011 |
| WO | 2013134273 | 9/2013 |
| WO | 2014058516 | 4/2014 |
| WO | 2016151367 | 9/2016 |
| WO | 2016181195 | 11/2016 |
| WO | 2016196274 | 12/2016 |
| WO | 2019048674 | 3/2019 |
| WO | 2019193608 | 10/2019 |
| WO | 2020089227 | 5/2020 |
| WO | 2020127928 | 6/2020 |
| WO | 2021135596 | 7/2021 |
| WO | 2023028252 | 3/2023 |
| WO | 2024069644 | 4/2024 |

OTHER PUBLICATIONS

Krupnik et al.; Iron-carbohydrate complexes treating iron anaemia: Understanding the nano-structure and interactions with proteins through orthogonal characterisation. J Control Release. Apr. 2024;368:566-579. doi: 10.1016/j.jconrel.2024.02.044. Epub Mar. 14, 2024. (2024).

Iron Sucrose Injection, Insert, DocId: GUID-E5748F79-5356-4F6F-991E-9B540E4B8D6A_5_en-US, DOI: https://doi.org/10.31003/USPNF_M42475_05_01, DOI Ref: 7czy7, Printed from: https://online.uspnf.com/uspnf/document/1_GUID-E5748F79-5356-4F6F-991E-9B540E4B8D6A_5_en-US (2025).

Venofer (iron sucrose) injection, for intravenous use Initial U.S. Approval: 2000, Revised Jun. 2022.

International Search Report for International application No. PCT/US2026/017662 dated Jun. 18, 2026, 3 pages.

International Written Opinion for International application No. PCT/US2026/017662 dated Jun. 18, 2026, 8 pages.

* cited by examiner

FIG. 2

| Timepoint (days) | 0 | 7 | 14 |
|---|---|---|---|
| pH | 5.52 | 4.78 | 4.71 |
| Z-average (nm) | 24.89 | 24.61 | - |

FIG. 3

| Method | Injectafer® 50 mg/mL | T=0 | T=7D 25°C | T=1M 25°C | T=1M 5°C |
|---|---|---|---|---|---|
| pH | 5.78 | 5.48 | 5.13 | 5.05 | 5.14 |
| Z-average (nm) | 24.77 | 24.32 | 24.34 | 24.45 | 24.37 |
| PDI | 0.080 | 0.076 | 0.063 | 0.090 | 0.073 |
| Zeta potential (mV) | 1.59 | -0.36 | -1.05 | -0.85 | -0.12 |
| Kinetic degradation T75 (min) | 42.7 | 44.9 | 40.9 | 39.6 | 40.8 |
| Kinetic degradation T50 (min) | 110.2 | 119.0 | 104.9 | 97.9 | 100.7 |
| Molecular Weight Comparison | 1.00 | - | - | 0.95 | 0.95 |

FIG. 4

| Diluent | 0.9% saline | | | | 5% Dextrose | | | | 0.9% saline + 10% maltodextrin | | | |
|---|---|---|---|---|---|---|---|---|---|---|---|---|
| **Method** | **0hr** | **4hr** | **3D** | **7D** | **0hr** | **4hr** | **3D** | **7D** | **0hr** | **4hr** | **3D** | **7D** |
| pH | 5.81 | - | 5.51 | 5.48 | 6.63 | - | 5.08 | 4.95 | 5.83 | - | 5.29 | 5.19 |
| Z-average (nm) | 24.82 | - | 24.45 | 25.16 | 26.86 | - | 25.73 | 25.78 | 51.35 | - | 27.98 | 36.43 |
| PDI | 0.080 | - | 0.078 | 0.106 | 0.086 | - | 0.091 | 0.080 | 0.311 | - | 0.301 | 0.437 |
| Zeta potential (mV) | -2.30 | - | -4.75 | -7.61 | -4.35 | - | -2.01 | -2.43 | -0.77 | - | -3.42 | -2.98 |
| | **0hr** | **4hr** | **1D** | **3D** | **0hr** | **4hr** | **1D** | **3D** | **0hr** | **4hr** | **1D** | **3D** |
| Kinetic degradation T75 (min) | 44.4 | 44.7 | 45.5 | 45.5 | 42.8 | 46.3 | 47.7 | 47.0 | 56.2 | 58.1 | 60.5 | 60.5 |
| Kinetic degradation T50 (min) | 119.8 | 117.5 | 119.4 | 121.7 | 112.6 | 124.3 | 129.1 | 126.0 | - | - | - | - |
| Iron Assay (mg/mL) | - | - | - | 2.80 | - | - | - | 2.73 | - | - | - | 2.24 |

FIG. 5

| Diluent | 0.9% saline | | | 5% Dextrose | | | 0.9% saline + 10% maltodextrin | | |
|---|---|---|---|---|---|---|---|---|---|
| Method | 0hr | 3D | 7D | 0hr | 3D | 7D | 0hr | 3D | 7D |
| pH | 5.74 | 5.60 | 5.51 | 6.76 | 6.57 | 6.61 | 6.31 | 5.79 | 5.54 |
| Z-average (nm) | 31.20 | 30.39 | 32.30 | 37.26 | 31.95 | 31.81 | 65.12 | 31.32 | 31.96 |
| PDI | 0.107 | 0.109 | 0.164 | 0.137 | 0.141 | 0.145 | 0.225 | 0.184 | 0.174 |
| Zeta potential (mV) | -2.03 | -3.33 | -3.88 | -3.89 | -7.89 | -9.01 | -1.07 | -3.94 | -4.23 |

FIG. 6

| Diluent | 0.9% saline | | | 5% Dextrose | |
|---|---|---|---|---|---|
| Sterilization Cycles | 1x | 2x | 4x | 1x | 2x |
| pH | 5.80 | 5.60 | 5.54 | 6.49 | 6.69 |
| Z-average (nm) | 29.49 | 31.31 | 35.45 | 37.49 | 99.63 |
| PDI | 0.103 | 0.109 | 0.122 | 0.138 | 0.187 |
| Zeta potential (mV) | -2.49 | -3.56 | -3.63 | -8.37 | -8.90 |
| Kinetic degradation T75 (min) | 60.0 | - | 50.5 | - | - |
| Kinetic degradation T50 (min) | 179.0 | - | 165.9 | - | - |
| Iron Assay (mg/mL) | 2.65 | - | 2.28 | - | - |

FIG. 7

| Container type | PVC | PP/PA/PE | Unconditioned in glass |
|---|---|---|---|
| pH | 4.94 | 4.98 | - |
| Z-average (nm) | 29.89 | 29.65 | - |
| PDI | 0.098 | 0.097 | - |
| Zeta potential (mV) | -1.69 | -0.83 | - |
| Kinetic degradation T75 (min) | 64.2 | 50.0 | 73.6 |
| Kinetic degradation T50 (min) | - | 139.6 | - |
| Iron Assay (mg/mL) | 2.32 | 2.89 | 2.77 |

FIG. 8

| | Container Type | Control in Glass (T=0) | PE-Based Container #1 | PE-Based Container #2 | PVC | PP/PA/PE |
|---|---|---|---|---|---|---|
| 6W 40C | Iron assay (mg/mL) | 2.77 | 2.84 | 2.82 | 4.00 | 2.85 |
| | Percent label claim | 100.0 | 102.4 | 101.8 | 144.6 | 102.7 |
| 3M 25C | Iron assay (mg/mL) | 2.77 | 3.02 | 2.76 | 3.22 | 2.76 |
| | Percent label claim | 100.0 | 109.1 | 99.5 | 116.2 | 99.8 |
| 3M 40C | Iron assay (mg/mL) | 2.77 | 2.79 | 2.80 | 6.89 | 3.00 |
| | Percent label claim | 100.0 | 100.8 | 101.2 | 248.9 | 108.5 |
| 6M 25C | Iron assay (mg/mL) | 2.77 | 2.84 | 2.75 | - | - |
| | Percent label claim | 100.0 | 102.4 | 99.4 | - | - |
| 6M 40C | Iron assay (mg/mL) | 2.77 | 3.42 | 2.86 | - | - |
| | Percent label claim | 100.0 | 123.3 | 103.2 | - | - |

FIG. 9

| pH Adjustment | No readjustment | pH 6.0 | pH 6.5 | pH 7.0 |
|---|---|---|---|---|
| pH | 5.27 | 5.77 | 6.20 | 6.67 |
| Z-average (nm) | 25.25 | 24.61 | 25.02 | 24.96 |
| PDI | 0.079 | 0.074 | 0.110 | 0.108 |
| Zeta Potential (mV) | -2.68 | -3.50 | -7.78 | -6.10 |
| Kinetic Degradation T75 (min) | 63.4 | 56.1 | 64.7 | 65.9 |
| Kinetic Degradation T50 (min) | - | 161.2 | - | - |
| Iron Assay (mg/mL) | 2.75 | 2.76 | 2.72 | 2.71 |

FIG. 10

| **Timepoint** | **1 Month** | | | **2 Months** |
|---|---|---|---|---|
| Storage Temperature | **25 °C** | **40 °C** | **55 °C** | **55 °C** |
| pH | 4.86 | 4.78 | 4.60 | 4.76 |
| Z-average (nm) | 24.43 | 24.15 | 23.21 | 23.63 |
| PDI | 0.103 | 0.104 | 0.069 | 0.089 |
| Zeta Potential (mV) | -1.23 | -1.16 | -1.06 | -2.09 |
| Kinetic Degradation T75 (min) | 44.7 | 49.7 | 56.1 | 58.1 |
| Kinetic Degradation T50 (min) | 114.5 | 131.2 | 144.9 | 146.0 |
| Iron Assay (mg/mL) | 2.93 | 2.92 | 2.91 | 2.97 |
| **MW Comparison** | 0.90 | 0.91 | 0.91 | 0.93 |

PHARMACEUTICALLY ACCEPTABLE READY-TO-USE FERRIC CARBOXYMALTOSE COMPOSITIONS

TECHNICAL FIELD

The present disclosure relates to ferric carboxymaltose formulations, for example, ready-to-use pharmaceutically acceptable formulations suitable for parenteral administration and stable at room-temperature (RT) for at least one month, preferably at least three months, more preferably at least six months, even more preferably at least 1 year, even more preferably at least 2 years.

BACKGROUND

Ferric Carboxymaltose (FCM) is an intravenous injection used to treat iron deficiency anemia in adult patients that have an intolerance to oral iron or non-dialysis dependent chronic kidney disease. INJECTAFER® is the currently available liquid vial product in the United States and is approved as single dose vials of 2 mL (100 mg iron), 10 mL (500 mg iron), 15 mL (750 mg iron) and 20 mL (1000 mg iron). However, the slow intravenous push should be given at a maximum rate of 100 mg elemental iron per minute (10 minutes for the maximum daily dose of 1000 mg), and the preparation of the diluted form requires the use of needles and takes additional time. According to the prescribing information, INJECTAFER® is stable for 72 hours once diluted.

SUMMARY

To the best knowledge of applicant, iron carbohydrate drugs are not available in a premixed, ready-to-use presentation. Additionally, current products are provided in glass vials and are not available in a flexible container. To address these disadvantages, some embodiments of the present disclosure provide a ferric carboxymaltose solution in a ready-to-use flexible container for immediate infusion without any further preparation steps. The ready-to-use ferric carboxymaltose premix improves clinician workflow efficiency and clinician and patient safety, for example by eliminating the need for dilution and thereby reducing medication errors.

BRIEF DESCRIPTION OF THE DRAWINGS

FIG. 2 is a table showing pH and particle size distribution z-average of 3 mg/ml INJECTAFER® in NS for 14 days in the experimental examples disclosed herein.

FIG. 3 is a table of results from INJECTAFER® in NS stored up to 1M in the experimental examples disclosed herein. Molecular weight data are presented as a comparison between the measured value for the test article and the measured value of an INJECTAFER® comparator within the same run.

FIG. 4 is a table of results from ferric carboxymaltose (FCM) formulations sterilized at 50 mg/mL and then diluted in 0.9% saline, 5% dextrose and 0.9% saline with 10% maltodextrin in the experimental examples disclosed herein. Initial measurements before storage for z-average, PDI and zeta potential were acquired at 3 mg/ml rather than the typical analytical concentration of 0.4 mg/mL.

FIG. 5 is a table of results from FCM formulations made at 3 mg/mL directly in 0.9% saline, 5% dextrose and 0.9% saline with 10% maltodextrin, then sterilized, in the experimental examples disclosed herein.

FIG. 6 is a table of data for impact of additional sterilization cycles of FCM formulations in NS and D5W in the experimental examples disclosed herein.

FIG. 7 is a table of data from sterilization of 3 mg/mL FCM in NS in PVC and PP/PA/PE in the experimental examples disclosed herein.

FIG. 8 is a table of iron assay data of FCM formulations from 6 weeks to 6 months in flexible containers in the experimental examples disclosed herein. "Percent label claim" describes the percentage comparison to the assay value measured in the glass control.

FIG. 9 is a table of data from readjustment of pH after FCM dilution in NS in the experimental examples disclosed herein.

FIG. 10 is a table of data from sterilization and storage of FCM formulations at 25° C., 40° C. and 55° C. in the experimental examples disclosed herein.

DETAILED DESCRIPTION

Definitions

Figure 1:
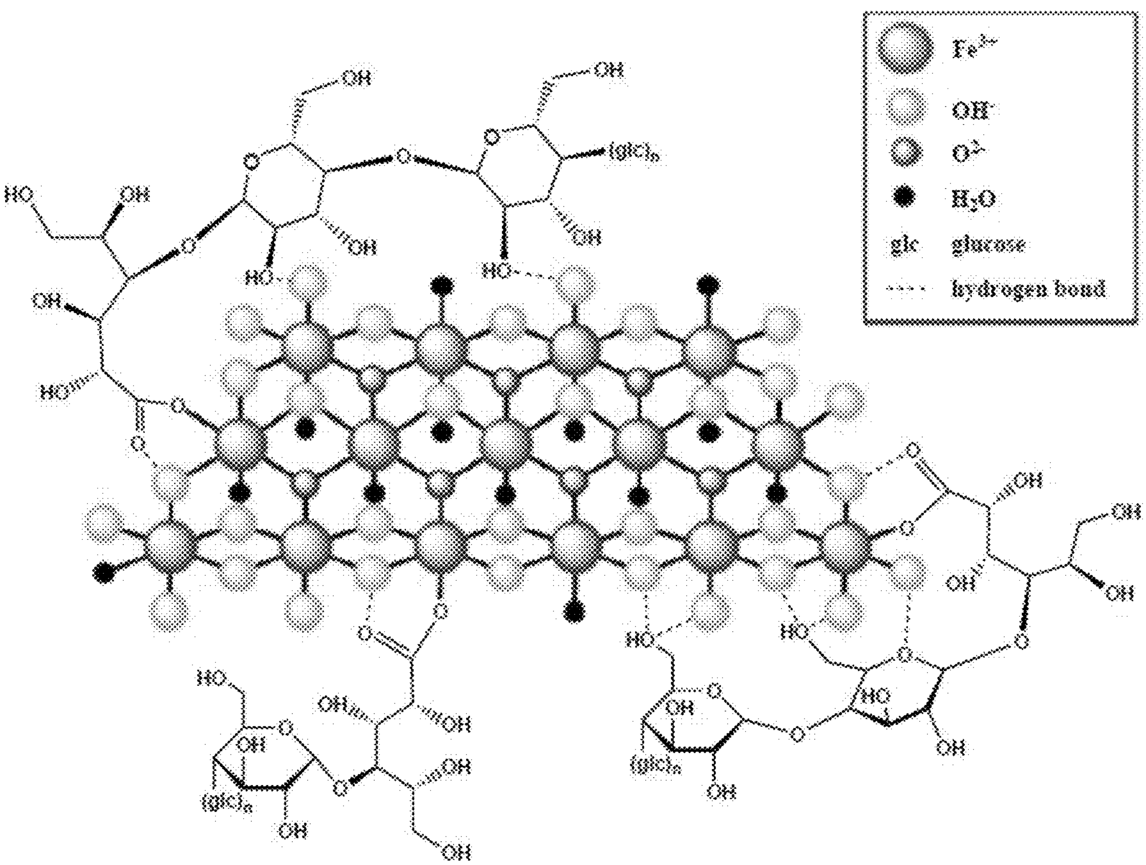
FIG. 1 shows the chemical structure of ferric carboxymaltose: $[FeO_x(OH)_y(H_2O)_z]_n[\{(C_6H_{10}O_5)_m(C_6H_{12}O_7)\}_l]_k$, where $n \approx 10^3$, $m \approx 8$, $l=11$, and $k=4$ (l represents the mean branching degree of the ligand).

Some definitions are provided hereafter. Nevertheless, definitions may be located in the "Embodiments" section below, and the above header "Definitions" does not mean that such disclosures in the "Embodiments" section are not definitions.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

All numerical ranges herein should be understood to include all integers, whole or fractions, within the range. Furthermore, a range defined "between" two endpoint numbers includes those two endpoint numbers. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the total weight of the composition unless expressed otherwise. When reference herein is made to the pH, values correspond to pH measured at about 25° C. with standard equipment.

As used in this disclosure and the appended claims, the singular forms "a," "an" and "the" include plural referents unless the context clearly dictates otherwise. Thus, for example, reference to "a pH adjustment agent" or "the pH adjustment agent" includes two or more pH adjustment agents.

The words "comprise," "comprises" and "comprising" are to be interpreted inclusively rather than exclusively. Likewise, the terms "include," "including," "containing" and "having" should all be construed to be inclusive, unless such a construction is clearly prohibited from the context. Further in this regard, these terms specify the presence of the stated features but not preclude the presence of additional or further features.

Nevertheless, the compositions and methods disclosed herein may lack any element that is not specifically disclosed herein. Thus, a disclosure of an embodiment using the term "comprising" is (i) a disclosure of embodiments having the identified components or steps and also additional components or steps, (ii) a disclosure of embodiments "consisting essentially of" the identified components or steps, and (iii) a disclosure of embodiments "consisting of" the identified components or steps. Any embodiment disclosed herein can be combined with any other embodiment disclosed herein.

The term "and/or" used in the context of "X and/or Y" should be interpreted as "X," or "Y," or "X and Y." Similarly, "at least one of X or Y" should be interpreted as "X," or "Y," or "X and Y." For example, "at least one of hydrochloric acid or sodium hydroxide" should be interpreted as "hydrochloric acid," or "sodium hydroxide," or "both hydrochloric acid and sodium hydroxide."

Where used herein, the terms "example" and "such as," particularly when followed by a listing of terms, are merely exemplary and illustrative and should not be deemed to be exclusive or comprehensive.

A "subject," "patient" or "individual" is a mammal, preferably a human. As used herein, an "effective amount" is an amount that prevents a deficiency, treats a disease or medical condition in an individual, or, more generally, reduces symptoms, manages progression of the disease, or provides a nutritional, physiological, or medical benefit to the individual.

The terms "treatment" and "treat" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The terms "treatment" and "treat" do not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment" and "treat" are also intended to include the potentiation or otherwise enhancement of one or more primary prophylactic or therapeutic measures. As non-limiting examples, a treatment can be performed by a patient, a caregiver, a doctor, a nurse, or another healthcare professional.

The term "unit dosage form," as used herein, refers to physically discrete units suitable as unitary dosages for human and animal subjects, each unit containing a predetermined quantity of the composition disclosed herein in amount sufficient to produce the desired effect, in association with a pharmaceutically acceptable diluent, carrier or vehicle. The specifications for the unit dosage form depend on the particular compounds employed, the effect to be achieved, and the pharmacodynamics associated with each compound in the host.

The term "pharmaceutically acceptable" and "pharmaceutically suitable" as used herein refers to substances that do not cause substantial adverse allergic or immunological reactions when administered to a subject, and preferably satisfies the FDA's product specific guidance for similarity in physico-chemical properties and pK as defined by bioequivalence in humans.

As used herein, a "ready-to-use" composition can be administered parenterally without any further compounding, dilution, or processing and preferably is formulated and packaged in a sealed container, such as a pre-filled flexible container such as a pre-filled flexible bag. The composition can be frozen and yet still considered ready-to-use if no further compounding, dilution or processing is needed prior to administration.

As used herein, "aseptically filled" and "aseptically prepared" are interchangeable and mean the ready-to-use pharmaceutically acceptable ferric carboxymaltose premix composition and the container are separately sterilized. Then the ready-to-use pharmaceutically acceptable ferric carboxymaltose premix composition is filled into the container in a sterile environment, and heat treatment is not applied to the ready-to-use pharmaceutically acceptable ferric carboxymaltose premix composition during the filling into the container and not applied after the filling into the container. In some embodiments, aseptic filling/preparation comprises the composition having been sterile filtered, for example through one or more filters having a pore size of 0.2 micron. "Terminal sterilization" means sterilization of a composition in its final container, such as by autoclaving.

As used herein, "room temperature" means about 25° C.

The terms "saline" and "sodium chloride" are used interchangeably herein.

Embodiments

Without being bound by any theory, applicant believes that addition of thermal energy rearranges colloids by adding or subtracting cores in a time, pH, and temperature dependent way, thereby influencing the particle size distribution z-average of the colloids. High temperatures change sugar chemistry and hydrogen bonding, influencing breakdown speed. Applicant identified a method that controls both effects, and also reduces the molecular weight (e.g., toward a target of 150,000 Da), to thereby achieve a pharmaceutically suitable ready-to-use ferric carboxymaltose premix composition that is stable in a sealed container at room-temperature (RT) for at least one month, preferably at least three months, most preferably at least six months.

A preferred embodiment of the method comprises adjusting the pH of a ferric carboxymaltose concentrate to between 5.0 and 7.0; subjecting the pH-adjusted concentrate to addition of thermal energy at about 132° C. or less, for example about 123° C. or less, such as about 40° C. to about 123° C., for about 2 hours to about one week, such as about 2 hours to about 72 hours; diluting the heat-treated concentrate in the presence of sodium chloride and adjusting the pH between 5.0 and 7.0; aseptically filling the composition into a container; and sealing the container.

The pharmaceutically suitable ready-to-use ferric carboxymaltose premix composition may be a single use premix which is a sterile, stable and ready-to-use aqueous solution for parenteral administration, for example intravenous (IV) administration such as IV infusion, and requires no dilution prior to parenteral administration. The container may be sealed with the pharmaceutically suitable ready-to-use ferric carboxymaltose premix composition within the container and then stored, for example at the shelf-life conditions disclosed herein.

Accordingly, an aspect of the present disclosure is a pharmaceutical product comprising a sealed container and further comprising a pharmaceutically suitable ready-to-use ferric carboxymaltose premix composition in the sealed container, the pharmaceutically suitable ready-to-use ferric carboxymaltose premix composition comprising water, sodium chloride, and ferric carboxymaltose in an amount that comprises about 2.0 mg to about 4.0 mg elemental iron/mL of the composition, preferably about 3.0 mg elemental iron/mL of the composition, wherein the pharmaceutically suitable ready-to-use ferric carboxymaltose premix composition is stable in the sealed container at room-temperature (RT) for at least one month, preferably at least three months, more preferably at least six months, even more preferably at least 1 year, and most preferably at least 2 years.

As used herein, "stable" means that the composition has a starting pH between 5 and 7 and maintains a pH within this range of 5 to 7 during storage in a sealed container at room-temperature (RT) storage for at least one month, preferably at least three months, more preferably at least six months, even more preferably at least 1 year, and most preferably at least 2 years. For example, a particularly preferred embodiment has a starting pH of about 6.0 and maintains a pH within a range of 5.0 to about 6.0, preferably 5.2-5.8, during storage in a sealed container at room-temperature storage for at least one month, preferably at least three months, more preferably at least six months, even more preferably at least 1 year, and most preferably at least 2 years.

In some embodiments, the storage is at 5° C. for a time period up to two years, and/or storage at 25° C. (RT) for a time period up to one year or two years.

Additionally or alternatively, stability of the composition may be measured by kinetic degradation. Specifically, T75 is the time for 75% of the elemental iron to be present in colloids/aggregates, and 25% of the elemental iron released from colloids/aggregates, after starting at about 99% in colloids/aggregates; T50 is the time for 50% of the elemental iron to be present in colloids/aggregates, and 50% of the iron released from colloids/aggregates, after starting at about 99% in colloids/aggregates. As used herein, a "stable" composition as measured by kinetic degradation has T75 of 37-65 minutes and/or T50 of 94-180 minutes.

Preferably the composition is suitable for parenteral administration such as intravenous infusion; for example, preferably the water is water-for-injection (WFI).

In some embodiments, the sealed container comprises a flexible bag. In a particularly preferred non-limiting embodiment, the sealed container such as a flexible bag contains a unit dosage form of the ready-to-use ferric carboxymaltose premix which is about 50 mL to about 500 mL, for example about 250 mL, and comprises an amount of the ferric carboxymaltose that comprises about 100 mg to about 1000 mg elemental iron, preferably about 500 mg to about 1000 mg elemental iron, most preferably about 750 mg elemental iron.

In other embodiments, the sealed container contains a unit dosage form of the ready-to-use ferric carboxymaltose premix composition which is about 50 mL and comprises an amount of the ferric carboxymaltose that comprises about 100 mg elemental iron.

In some embodiments, the sodium chloride is about 0.9% of the composition.

Preferably, the pharmaceutically suitable ready-to-use ferric carboxymaltose premix composition further comprises at least one pH adjusting agent, which is one or more acids or bases such as hydrochloric acid (HCl), sodium hydroxide (NaOH), or a similar pH adjustor known in the art. In a particularly preferred non-limiting embodiment, the composition comprises a total amount of the at least one pH adjusting agent effective for the composition to have a pH of about 5.0 to about 7.0, preferably about 6.0.

Preferably, the ferric carboxymaltose has a particle size distribution z-average of about 22 nm to about 28 nm, preferably about 23 nm to about 27 nm, preferably about 24 nm to about 26 nm, most preferably about 25 nm, and/or has a D50 size of about 18 nm to about 22 nm, preferably about 19 nm to about 21 nm, most preferably about 20 nm.

In some embodiments, the pharmaceutically suitable ready-to-use ferric carboxymaltose premix composition does not contain any buffering agent. In a particularly preferred non-limiting embodiment, the pharmaceutically suitable ready-to-use ferric carboxymaltose premix composition consists or consists essentially of the water, the ferric carboxymaltose, the sodium chloride, the at least one pH adjusting agent, and optionally a buffering agent.

In a preferred embodiment, the pharmaceutically suitable ready-to-use ferric carboxymaltose premix composition has been aseptically filled into the container and has not been subjected to terminal sterilization in the container.

Non-limiting examples of the container include a flexible plastic container having an inner surface contacting the ready-to-use pharmaceutically suitable ferric carboxymaltose premix composition, wherein the inner surface may be made of a plastic material, or a layer of plastic material. Preferred plastic materials for the inner surface contacting the ready-to-use pharmaceutically suitable ferric carboxymaltose premix composition include polyethylene (PE), linear low density polyethylene (LLDPE), polyvinyl chloride (PVC), polypropylene (PP), or a copolymer, modified polymer, or copolymer of the preceding polymer types. For example, the inner surface of the flexible container may be made of a flexible PE or LLDPE. In such embodiments, it was surprisingly found that the iron does not adsorb, or absorb into, the LLDPE surface of the flexible plastic container.

In some embodiments, the flexible container is a GALAXY® single dose flexible container intended for intravenous drug infusion, for example having a capacity of about 250 mL. The GALAXY® flexible container may be made of a single polymeric layer or multiple layers bonded together or co-extruded. These film layers may comprise polymers such as, but not limited to, polyolefins, polyethers, and polyamides (nylon, for example). The inner surface of the GALAXY® flexible container may be polyethylene (PE) or a layer of PE, which contacts the drug solution inside the bag.

Another aspect of the present disclosure is a method of preparing a pharmaceutical product comprising a sealed container and further comprising a pharmaceutically suitable ready-to-use ferric carboxymaltose premix composition in the sealed container. The method comprises:

(i) dissolving ferric carboxymaltose in water to form a concentrate, for example the concentrate comprising an amount of the ferric carboxymaltose that comprises about 10.0 mg to about 75.00 mg elemental iron/mL of the concentrate, such as about 50.0 mg elemental iron/mL of the concentrate;

(ii) adjusting the pH of the concentrate to 5.0 to 7.0, preferably about 6.0, for example with hydrochloric acid;

(iii) subjecting the pH-adjusted concentrate to addition of thermal energy, for example at about 132° C. or less, for example about 123° C. or less, such as about 40° C. to about 123° C., for about 2 hours to about one week, such as about 2 hours to about 72 hours;

(iv) diluting the heat-treated concentrate in the presence of sodium chloride, for example to a concentration of the ferric carboxymaltose that comprises about 2.0 mg to about 4.0 mg elemental iron/mL of the diluted composition, preferably about 3.0 mg elemental iron/mL of the diluted composition, and adjusting the pH to 5.0 to 7.0, preferably about 6.0, for example with sodium hydroxide, to form the pharmaceutically suitable ready-to-use ferric carboxymaltose premix composition;

(v) aseptically filling the pharmaceutically suitable ready-to-use ferric carboxymaltose premix composition into the container; and (vi) sealing the container.

In some embodiments, the ferric carboxymaltose dissolved into the water in step (i) has a particle size distribution z-average of about 30 nm to about 39 nm, for example about 30 nm to about 38 nm, such as about 32 nm, and the ferric carboxymaltose in the pharmaceutically suitable ready-to-use ferric carboxymaltose premix composition formed in step (iv) has a particle size distribution z-average of about 22 nm to about 28 nm, preferably about 23 nm to about 27 nm, preferably about 24 nm to about 26 nm, most preferably about 25 nm, and/or has a D50 size of about 18 nm to about 22 nm, preferably about 19 nm to about 21 nm, most preferably about 20 nm.

Preferably the method further comprises filtering the composition between steps (iv) and (v), for example through a 0.2 μm filter.

The adjusting the pH to 5.0 to 7.0, preferably about 6.0, to form the pharmaceutically suitable ready-to-use ferric carboxymaltose premix composition in step (iv) may occur at one or more times selected from the group consisting of (a) before the diluting of the heat-treated concentrate in the presence of sodium chloride, (b) during the diluting of the heat-treated concentrate in the presence of sodium chloride, and/or after the diluting of the heat-treated concentrate in the presence of sodium chloride.

In some embodiments, the method uses a system comprising a first vessel and further comprising a second vessel. For example, an embodiment of the method performs at least step (iii) in the first vessel, preferably performs at least steps (ii) and (iii) in the first vessel, and more preferably performs steps (i)-(iii) in the first vessel. The method may further comprise transferring the heat-treated concentrate formed by step (iii) from the first vessel into the second vessel. The method preferably comprises performing step (iv) in the second vessel. The first vessel may have a smaller volume than the second vessel.

Yet another aspect of the present disclosure is a method of treating a patient having one or more diseases, disorders or conditions characterized by iron deficiency or dysfunctional iron metabolism. The method comprises parenteral administration of an effective amount of any of the ready-to-use ferric carboxymaltose premix compositions disclosed herein, for example from the container (e.g., a flexible bag) of any of the pharmaceutical products disclosed herein.

A further aspect of the present disclosure is another method of treating a patient having one or more diseases, disorders or conditions characterized by iron deficiency or dysfunctional iron metabolism. The method comprises: (i) storing any of the pharmaceutical products disclosed herein (i.e., a sealed container and a pharmaceutically acceptable ready-to-use ferric carboxymaltose premix composition in the sealed container) for at least one month, or at least three months, of at least six months, for example at room temperature; and (ii) providing the pharmaceutical product to a patient with one or more diseases, disorders or conditions characterized by iron deficiency or dysfunctional iron metabolism. In some embodiments, the providing the pharmaceutical product to a patient comprises administering the pharmaceutically acceptable ready-to-use ferric carboxymaltose composition to the patient.

Suitable routes for parenteral administration include intravenous, subcutaneous, intradermal, intramuscular, intraarticular, and intrathecal. The ready-to-use ferric carboxymaltose premix composition is preferably administered by intravenous infusion.

There are many diseases, disorders or conditions characterized by iron deficiency or dysfunctional iron metabolism that can be treated with the injectable iron compositions described in this application. For example, in some embodiments, the disease, disorder, or condition is anemia, and, in some cases, the anemia is iron deficiency anemia. In other embodiments, the iron deficiency anemia is associated with chronic blood loss; acute blood loss; chronic kidney disease; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidal anti-inflammatory agents, or chronic ingestion of erythropoiesis stimulating agents or combinations thereof.

In various embodiments, the ready-to-use pharmaceutically acceptable ferric carboxymaltose compositions described herein may be used to treat an anemia which is anemia of chronic disease, such as for example, rheumatoid arthritis; cancer; Hodgkin's leukemia; non-Hodgkin's leukemia; anemia from chemotherapy; inflammatory bowel disease; ulcerative colitis; thyroiditis; hepatitis; systemic lupus erythematosus; polymyalgia rheumatica; scleroderma; mixed connective tissue disease; Sjogren's syndrome; congestive heart failure/cardiomyopathy; or idiopathic geriatric anemia.

In some instances, diseases, disorders or conditions characterized by iron deficiency or dysfunctional iron metabolism is an anemia that is due to impaired iron absorption or poor nutrition or the anemia is associated with Crohn's Disease; gastric surgery; ingestion of drug products that inhibit iron absorption; and chronic use of calcium. In yet other instances, the method of treatment described in this application treats anemia. In some embodiments, the anemia is an iron deficiency anemia, such as that associated with chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidal anti-inflammatory agents, or chronic ingestion of erythropoiesis stimulating agents. In some aspects, the anemia is anemia of chronic disease, such as rheumatoid arthritis; cancer; Hodgkin's leukemia; non-Hodgkin's leukemia; cancer chemotherapy; inflammatory bowel disease; ulcerative colitis thyroiditis; hepatitis; systemic lupus erythematosus; polymyalgia rheumatica; scleroderma; mixed connective tissue disease; Sjogren's syndrome; congestive heart failure/cardiomyopathy; or idiopathic geriatric anemia. In some embodiments, the anemia is due to impaired iron absorption or poor nutrition, such as anemia associated with Crohn's Disease; gastric surgery; ingestion of drug products that inhibit iron absorption; and chronic use of calcium. In various embodiments, the method treats restless leg syndrome; blood donation; Parkinson's disease; hair loss; or attention deficit disorder.

Examples

The following non-limiting examples support the concept of ready-to-use pharmaceutically acceptable ferric carboxymaltose compositions suitable for parenteral administration and stable at room-temperature (RT), as disclosed herein.

Test and Control Articles

The test articles included ferric carboxymaltose with varying diluents, concentrations, container types and formulation parameters. The control article was INJECTAFER® by American Regent, both at 50 mg/mL and diluted to 2-4 mg/mL in 0.9% saline as per prescribing information.

Experimental/Study Design

Preparation of Test Articles

The test articles were formulated with the following steps:

1) Weighed out the appropriate amount of ferric carboxymaltose API to achieve desired concentration of elemental iron with the Iron Assay % value from the supplier Certificate of Analysis (COA) using Equation 1.

Equation 1: Amount of API Needed $$\text{Amount needed (g)} = (X\ \text{mg/mL} * 1\ \text{g/1000 mg} * Y\ \text{mL})/(\%\ \text{Iron}/100)$$

where X is the desired concentration in mg/mL, and Y is the desired number of mL.

2) Added the API to begin dissolving in a quantity of diluent that left sufficient volume for pH adjustment and eventual QS. Used a stir bar, heating to up to 40° C., and sonication as needed to visually dissolve the API material.

3) Used NaOH and/or HCl to adjust the pH of the solution to the target value.

4) Transferred the pH-adjusted solution to a volumetric flask and brought to the QS volume with diluent.

5) Optionally filtered through a 0.2 μm retention rated nylon filter and filled into desired container closure system. Some formulations were filtered at 50 mg/mL and some formulations were filtered at 3 mg/mL.

6) If the solution was filled into vials, nitrogen blanketed the vial headspace.

7) Optionally either terminal sterilization or storage at elevated temperature.

8) Optionally diluted solution to 3 mg/mL in 0.9% sodium chloride. If not already filtered, the 3 mg/mL formulations were filtered through a 0.2 μm retention rated nylon filter.

Testing

The particle size distribution (PSD) measurement is reported as the particle size distribution z-average in nm and polydispersity index (PDI). Each particle size measurement consists of three runs that are averaged per sample.

Unless otherwise specified, kinetic degradation is corrected using iron assay measurements on the same samples. Kinetic degradation is reported as T75 (number of minutes after which 25% of elemental iron has been released from the colloids) or T50 (number of minutes after which 50% of elemental iron has been released from the colloids).

Results for Control Article—50 mg/mL INJECTAFER®

Stability of Control Article in Saline

Initial testing assessed the pH and particle size of INJECTAFER® after dilution to 3 mg/mL in normal saline (NS) for up to 14 days, as shown in FIG. 2. The pH fell below the acceptable 5.0-7.0 range provided in the package insert by seven days after dilution. The particle size remained constant up to seven days after dilution.

A second series of experiments assessed the properties of INJECTAFER® at 3 mg/mL in NS for up to one month with a larger suite of experiments. The results are shown in FIG. 3. T=0 results were acquired on freshly opened vials in the several hours following dilution for pH, particle size distribution z-average, zeta potential and kinetic degradation measurements. Iron assay and molecular weight measurements were acquired on opened vials because they were not expected to change with oxygen exposure.

The particle size distribution z-average and molecular weight decreased slightly with storage time. The pH again dropped consistently over time to just over the product specification; the pH changed less with 5° C. storage than with 25° C. storage. The release rate became faster with longer storage time when compared to the INJECTAFER® 50 mg/mL control. This behavior may also indicate a stability-limiting parameter at 3 mg/mL in saline.

Evaluation of Diluents

The INJECTAFER® package insert indicates that the concentrated liquid should be diluted in 0.9% saline to a concentration of 2-4 mg/mL. Three diluents were evaluated for potential use in the premix product: 0.9% normal saline (NS), 5% dextrose (D5W) and 0.9% NS with 10% maltodextrin (NS+MD). Maltodextrin was evaluated because of potential compatibility with the carboxymaltose carbohydrate. Vials stored for the vial presentation formulation feasibility stability study were diluted to approximately 3 mg/mL in the three diluents. Additionally, formulations were made directly at 3 mg/ml in the diluents. All formulations for this experiment were adjusted to pH 7. Critical parameters were evaluated for up to 7 days. The results of this experiment are shown in FIGS. 4 and 5.

Maltodextrin was eliminated as a candidate diluent because of unpredictable behavior of particle size and aggregation, large polydispersity index (PDI), slow kinetic degradation rates, and lack of precedent for use in injectable products. For NS and D5W, behavior of the 50 mg/mL sterilized formulation diluted to 3 mg/mL was as expected with some exceptions: the pH of the formulation in dextrose dropped significantly over 7 days from 6.63 to 4.95.

For formulations made at 3 mg/mL in the diluents and then sterilized, the particle size distribution z-average in all three diluents was larger (at 30-32 nm) than when sterilized at 50 mg/mL. Additionally, the PDI was higher when formulated at 3 mg/mL and sterilized. These results indicated that there may be mechanistic differences when sterilized at 3 mg/mL or when sterilized in the presence of a tonicity adjuster such as sodium chloride, that result in an incorrect particle size.

It was observed during diluent testing that particle size and PDI were larger when the formulation was sterilized at 3 mg/ml than when sterilized at 50 mg/ml. The effects of sterilization were evaluated further in NS and D5W by performing multiple simultaneous sterilization cycles, where 1× cycle is sterilization at 250° F./121.1° C. for 20 minutes. Formulations were made at pH 6.5 at 3 mg/mL in NS and D5W and sterilized 1×, 2× and 4× times. These results are shown in FIG. 6.

For both diluents, the particle size distribution z-average and PDI increased with more sterilization cycles; in dextrose, the particle size reached 100 nm with 2× cycles and was not measured after 4× cycles because the material clearly precipitated. The kinetic degradation release rate improved slightly when compared to INJECTAFER® after 4× cycles in NS, indicating that there may be some change to the chemistry of the carbohydrate shell with additional thermal energy independent from the arrangement of iron cores.

Sterilization at 3 mg/mL in NS was assessed in a flexible container made of polyvinylchloride (PVC) and a flexible container made of a multilayer of polypropylene (PP), polyamide (PA) and polyethylene (PE). The formulations were made at 3 mg/ml at pH 6.5, filled into the bags and terminally sterilized at 250° F./121° C. for 20 minutes. FIG. 7 shows the results from this experiment as well as an unconditioned control glass.

The pH dropped to below the 5.0-7.0 specification for PVC and PP/PA/PE. The particle size distribution z-average was too high for both containers, and the kinetic degradation speed was at the high end of the 37-65 minute range in PVC. The kinetic degradation speed improved to the center of the range in PP/PA/PE. The kinetic degradation comparison improved in PP/PA/PE to around 10% slower than INJECTAFER®. Notably, the iron assay in PVC decreased to 2.3 mg/mL compared to the glass control of 2.8 mg/mL; it is possible that iron particles are being absorbed or adsorbed to the PVC bag. This effect was confirmed through energy dispersive spectroscopy, where iron signal was detected in a cross-section of the PVC film.

Based on the results of these two experiments, it was concluded that the FCM premix cannot be terminally sterilized at 3 mg/mL to achieve the correct properties.

Bag Interactions

Potential risks in the selection of a container closure system include loss of iron to the film of the bag as well as other changes to critical properties. A 6-month experiment was conducted to assess change in iron assay over time in various flexible containers including a flexible container made of polyvinylchloride (PVC) and a flexible container made of a multilayer of polypropylene (PP), polyamide (PA) and polyethylene (PE). The formulation did not undergo any thermal treatment before storage at 25° C. and 40° C., resulting in incorrect properties for PSD, molecular weight and kinetic degradation rate; as these data are not relevant to the final formulation, only iron assay will be assessed in this section. FIG. 8 provides iron assay data for the control in glass and samples in bags after storage from 6 weeks to 6 months.

There were no decreases in iron concentration for any of the container types. Increases in concentration, particularly for the flexible container made of PVC at 40° C. and the flexible container made of a multilayer of PP, PA and PE are likely due to water loss. These data suggest that there is likely no iron loss due to absorption or adsorption to the film in the bags as a function of storage time at various temperatures.

The studies discussed above determined that the premix cannot be terminally sterilized directly at 3 mg/mL in NS but that thermal treatment is required to achieve the correct properties. It was concluded that thermal treatment of the concentrate is required before dilution in 0.9% saline.

Re-Adjustment of pH after Dilution in NS

The next experiment assessed the effect of pH readjustment after dilution in NS. The concentrate was formulated at pH 6.0 and thermally treated. The formulation was then diluted to 3 mg/mL in 0.9% saline and readjusted to pH 6.0, pH 6.5 and pH 7.0. The vials were stored for at least 1 week at 25° C. before any measurements were collected to allow for equilibration.

The results are shown in FIG. 9. The pH of readjusted samples equilibrated to around 0.3 lower than the adjustment pH over 1 week, while the unadjusted sample decreased by 0.7 from the formulation pH of 6.0. The z-average was variable without a trend, which may be a result of instrument variability. The PDI was higher when readjusted to pH 6.5 and 7.0 than when readjusted to pH 6.0 or not readjusted. Zeta potential was slightly more negative for pH 6.5 and pH 7.0, but these changes may be within instrument variability. The kinetic degradation release rates were at the high end of the range for most conditions; the rate was closer to the center of the range at readjustment pH 6.0 with a T75 of 56 minutes.

This experiment demonstrated that readjusting the 3 mg/mL pH to 6.0, the same as the original 50 mg/mL formulation pH, resulted in a smaller decrease in pH over time and yielded similar results for other properties.

Sterilization and Storage at 25° C., 40° C. And 55° C.

Formulations at pH 6.0 were sterilized at 121° C. for 15 minutes, diluted to 3 mg/mL in NS and stored at 25° C., 40° C. and 55° C. to be measured over time (FIG. 10). This experiment is intended to assess whether drift over time in properties such as release rate could be mitigated by sterilization rather than addition of thermal energy at intermediate temperatures. Samples stored at 25° C. and 40° C. were measured after 1 month and samples stored at 55° C. were measured after 1 month and 2 months. The 55° C. storage temperature was used as accelerated storage.

The pH was not readjusted after dilution, so the pH decreased over time as expected. The pH was consistent across storage temperatures. Particle size decreased during storage at 55° C. when compared with 25° C. and 40° C., and the z-average remained the same after 2 months. Zeta potential and molecular weight were consistent across all storage temperatures and times.

The kinetic degradation release rate was slower from 25° C. to 40° C. to 55° C., with a spread of 20-25%. The rate for 55° C. storage continued to slow after 2 months. All rates were within the 37-65 minute range. While some actual physical or chemical changes may occur due to addition of thermal energy at 40° C. or 55° C., these data suggest that the release rate is likely to become slower over time for sterilized samples diluted in NS.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A pharmaceutical product comprising a sealed container and further comprising a pharmaceutically suitable ready-to-use ferric carboxymaltose premix composition in the sealed container, the pharmaceutically suitable ready-to-use ferric carboxymaltose premix composition comprising water, sodium chloride, and ferric carboxymaltose in an amount that comprises about 2.0 mg to about 4.0 mg elemental iron/mL of the composition, wherein the pharmaceutically suitable ready-to-use ferric carboxymaltose premix composition does not contain any buffering agent, wherein the pharmaceutically suitable ready-to-use ferric carboxymaltose premix composition is stable in the sealed container at room-temperature (RT) for at least one month.

2. The pharmaceutical product of claim 1, wherein the pharmaceutically suitable ready-to-use ferric carboxymaltose premix composition is suitable for parenteral administration.

3. The pharmaceutical product of claim 1, wherein the sealed container comprises a flexible bag.

4. The pharmaceutical product of claim 1, wherein the sealed container contains a unit dosage form of the ready-to-use ferric carboxymaltose premix composition which is about 250 mL and comprises an amount of the ferric carboxymaltose that comprises about 100 mg to about 1000 mg elemental iron.

5. The pharmaceutical product of claim 1, wherein the sealed container contains a unit dosage form of the ready-to-use ferric carboxymaltose premix composition which is about 50 mL and comprises an amount of the ferric carboxymaltose that comprises about 100 mg elemental iron.

6. The pharmaceutical product of claim 1, wherein the sodium chloride is about 0.9% of the composition.

7. The pharmaceutical product of claim 1, wherein the ferric carboxymaltose has a particle size distribution z-average of about 22 nm to about 28 nm.

8. The pharmaceutical product of claim 1, wherein the pharmaceutically suitable ready-to-use ferric carboxymaltose premix composition has been aseptically filled into the container and has not been subjected to terminal sterilization in the container.

* * * * *